United States Patent [19]
Weijand et al.

[11] Patent Number: 5,843,135
[45] Date of Patent: Dec. 1, 1998

[54] PACING SYSTEM WITH LEAD HAVING A SINGLE CONDUCTOR FOR CONNECTING TO PRESSURE SENSOR AND ELECTRODE

[75] Inventors: Koen J. Weijand, Hoensbroek; Robert Leinders, Limbricht, both of Netherlands

[73] Assignee: Medtronic, Inc., Minneapolis, Minn.

[21] Appl. No.: 954,043

[22] Filed: Oct. 20, 1997

[51] Int. Cl.$^6$ .................................................. A61N 1/362
[52] U.S. Cl. ............................................. 607/17; 607/122
[58] Field of Search .............................. 607/17, 122, 123, 607/119, 23, 9

[56] References Cited

U.S. PATENT DOCUMENTS

| | | |
|---|---|---|
| 4,432,372 | 2/1984 | Monroe . |
| 4,485,813 | 12/1984 | Anderson et al. . |
| 4,566,456 | 1/1986 | Koning et al. . |
| 4,708,143 | 11/1987 | Schroeppel . |
| 4,791,935 | 12/1988 | Baudino et al. . |
| 4,967,755 | 11/1990 | Pohndorf . |
| 5,275,171 | 1/1994 | Barcel ........................ 607/122 |
| 5,324,326 | 6/1994 | Lubin ......................... 607/122 |
| 5,336,253 | 8/1994 | Gordon et al. ............. 607/122 |
| 5,411,532 | 5/1995 | Mortazavi .................. 607/122 |

Primary Examiner—Scott M. Getzow
Attorney, Agent, or Firm—Michael J. Jaro; Harold Patton

[57] ABSTRACT

A pacing system is provided having a lead with a pressure transducer or other sensor, the lead being characterized by having only a single conductor connecting the pacemaker with the signals from the sensor and the signals to and from the lead tip electrode. A connecting circuit mounted in the lead near the distal end is powered by a low level alternating constant current square wave to provide multiplexed signals on the conductor. The lead connecting circuit comprises a switching device connected to a sensor, such as a piezoelectric pressure transducer, so that for positive current pulses delivered to the lead, the transducer output is added in series with any cardiac signal sensed by the tip electrode; while for negative currents the pressure transducer is isolated and only the tip electrode signal information is connected back to the pacemaker. The pacemaker contains processing circuitry for decoding the respective cardiac signals and pressure signals from the multiplexed signals.

20 Claims, 2 Drawing Sheets

PACING SYSTEM WITH LEAD HAVING A SINGLE CONDUCTOR FOR CONNECTING TO PRESSURE SENSOR AND ELECTRODE

FIELD OF THE INVENTION

This invention relates to cardiac pacing leads and, more particularly, leads incorporating a sensor for sensing pressure or another cardiac-related parameter.

BACKGROUND OF THE INVENTION

Cardiac pacing systems have become increasingly sophisticated in the ability to utilize sensor information for control of pacemaker performance. With the advent of rate responsive pacing, implantable pacemakers have utilized a variety of different types of sensors for obtaining rate-indicating parameters. Although some of such sensors are mounted in or on the pacemaker can, such as activity sensors, many sensors are located in the distal region of the lead, so as to be appropriately positioned within the heart chamber. For example, rate responsive pacemakers may incorporate sensors for monitoring blood pressure, respiration, pH, oxygen, etc. More recently, with the advent of microprocessors in pacemakers, which provide substantially increased data processing capability, sensors have also been used for obtaining signals to control other timing operations, accumulating diagnostic data, etc. Specifically, pressure transducers, e.g., piezoelectric transducers have been found to be desirable for obtaining both operational and diagnostic data. The pressure transducer is generally packaged in the distal region of the tip, located just back, or proximal from the tip electrode, so as to be in an appropriate position in the ventricle or atrium when the pacing electrode, or electrodes for a bipolar system, are placed in the heart chamber.

Incorporation of a sensor within a unipolar pacing lead has generally required plural conductors running the length of the lead, in order to provide proper electrical connection between the implanted pacemaker and the sensor on one hand, and between the pacemaker and the tip electrode; for a bipolar lead, an additional conductor is required. However, the more electrical conductors that are required in a lead, the greater potential for lead unreliability. Lead reliability remains a chronic problem, and anything that can be done to minimize the number of conductors required to run the length of the pacing lead is a step forward in terms of maximizing lead reliability.

Pacemaker designers have responded with several different arrangements for reducing the number of leads, but have not yet achieved a design that requires only one conductor in order to connect the pacemaker with both a sensor and the tip electrode. For example, in U.S. Pat. No. 4,432,372, a lead is shown providing a silicon-based piezoresistive pressure transducer, which has the electrical characteristics of a bridge circuit with the resistive values changing as a function of pressure. Two conductors are multiplexed by a switching circuit and capacitor, between the two functions of supplying power to the transducer and sensing the resulting changes in the resistivity. This reduces the lead conductors required just for the transducer from four to two. In U.S. Pat. No. 4,791,935, a lead is utilized incorporating an oxygen-sensing pacemaker. Multiplexing of conductors, using complex circuitry, allows for connection to the oxygen sensor and connection for bipolar pacing and sensing on three leads for a unipolar lead. Other arrangements have been disclosed in the patent art, but all require two or more leads for a unipolar lead. See, for example, U.S. Pat. No. 4,485,813, disclosing a clock-driven piezoelectric crystal and circuitry for recovering the information-carrying transducer signal; and U.S. Pat. No. 4,497,755, showing a pressure sensor with an FET in a source follower configuration but requiring an entirely separate lead conductor for connection to the tip electrode.

Consequently, it remains an object to provide a lead which incorporates a pressure sensor or similar transducer positioned toward the distal end for sensing a heart parameter, the lead having a safe arrangement enabling the use of only one conductor for providing a connection to both the sensor and a pacing/sensing electrode positioned at or about the distal tip of the lead.

SUMMARY OF THE INVENTION

It is an object of this invention to provide a pacing lead incorporating both a sensor, e.g., a pressure sensor, and an electrode for pacing and sensing, the lead being connected to a pacemaker which delivers pacing pulses to the electrode, the pacemaker also receiving and processing cardiac signals from the electrode and sensor information from the sensor.

Accordingly, there is provided a pacing system having a pacing lead with proximal and distal ends, having a transducer, suitably a pressure sensor, incorporated within the lead casing in the distal region, and a distal tip electrode for delivering pacing pulses and sensing cardiac signals when the distal end of the electrode is positioned in a heart chamber. A single conductor extends from the proximal end of the lead to the distal region, and provides the required electrical connection between the pacemaker and both the sensor and the tip electrode. A multiplexing arrangement is utilized for switchably connecting the pacemaker to receive signals carrying information from which respective cardiac signals and sensor signals can be derived. The pressure sensor, or other sensor, is connected within the lead to a switching device, suitably an N MOSFET, so that when the combination of sensor and switch is driven with the constant current in one direction, the sensor is effectively connected between the tip electrode and the pacemaker; whereas when the constant current is in the opposite direction, the switch effectively isolates the sensor so that only cardiac signal information is delivered to the pacemaker. The square wave of a constant current generator in the pacemaker provides a low amplitude drive signal which is connected through to the sensor/switching device configuration to provide the desired multiplexing. Processing circuitry within the pacemaker enables deriving respective sensor and cardiac signal information from signals sensed during alternate cycles of the alternating current signal. By the above arrangement, the lead requires only one conductor for a unipolar system, or two for a bipolar system, and provides AC coupling to the sensor such as creates an inherent safety advantage since the multiplexing current is well below the cardiac stimulus threshold and safety current limit.

DESCRIPTION OF THE PREFERRED EMBODIMENTS

Figure 1:
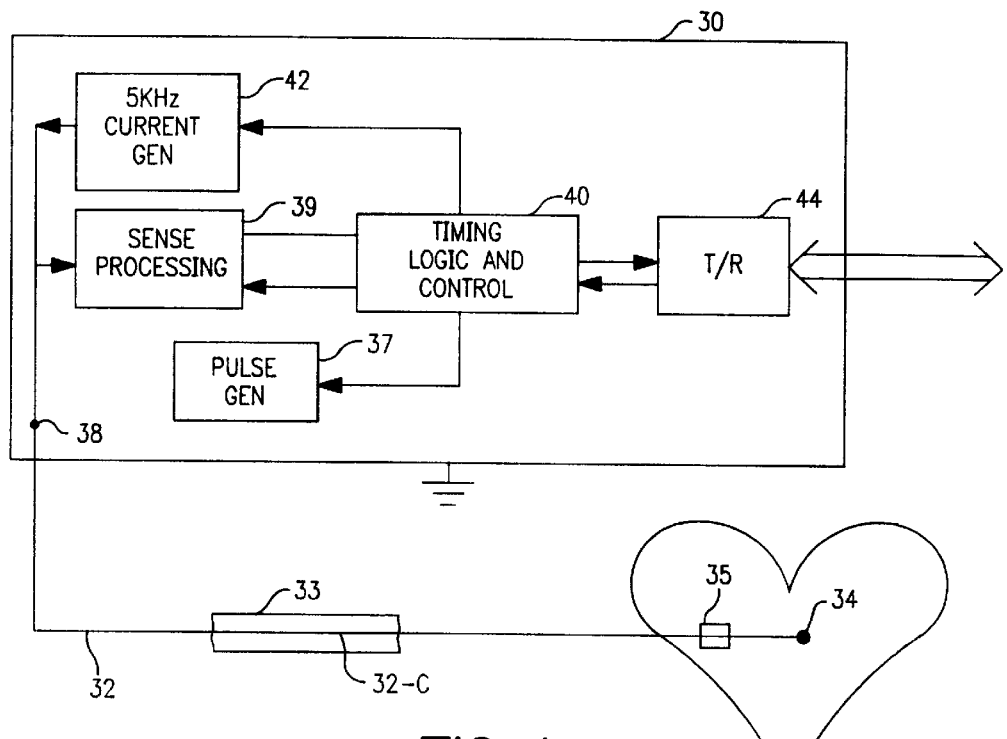
FIG. 1 is a schematic block diagram showing the primary components of a pacemaker system in accordance with this invention.

Referring now to FIG. 1, there is shown a block diagram representing a pacemaker device 30, connected at an output 38 to a lead 32. The lead 32 extends into the heart, and as shown diagrammatically has a tip electrode 34 and a combined sensor and switching circuit 35. As provided by this invention, lead 32 need have only a single conductor 32-C in order to send pacing pulses to tip electrode 34 and to receive cardiac signals and sensor information back from the heart. For a unipolar pacing system, the pacemaker case, or can, is system ground, providing the closed electrical loop; a bipolar arrangement (not shown) may be employed where the lead has a second conductor connected to a second electrode, suitably a ring electrode displaced just proximally from the tip electrode 34. The lead has a casing, or outer tubing 33 which runs the length of the lead from its proximal end where it connects to output 38, to its distal end where tip electrode 34 is positioned.

The pacemaker has a pulse generator 37 which provides output pulses connected through output terminal 38 to lead 32 in a known manner. Pulse generator 37 is suitably controlled by signals from timing, logic and control block 40, in a known manner. Block 40 suitably contains a microprocessor or equivalent, as well as software, and can contain any combination of hardware and software for performing the conventional pacemaker functions of timing, logic and other functions, including storage of diagnostic data. The circuitry and software of block 40 is suitably in two-way communication with a transmit and receive circuit, indicated at block 44 as T/R, which in turn is in telemetric communication with an external programmer. Sense processing circuitry is shown at 39, which receives signals from lead 32, as is discussed in more detail below. This circuitry suitably contains two sense amplifiers of conventional configuration for receiving cardiac signals, and additionally contains other circuitry for enabling the separation of cardiac and sensor information in accordance with this invention. The pressure and cardiac signals which are developed through circuitry 39 are transmitted to block 40, for use in continued operation of pacemaker functions and/or for data collection purposes. Additionally, a square wave current generator, indicated at 42, is operated under control of block 40, and provides an output that is connected through terminal 38 to lead 32, as discussed below.

Figure 2:
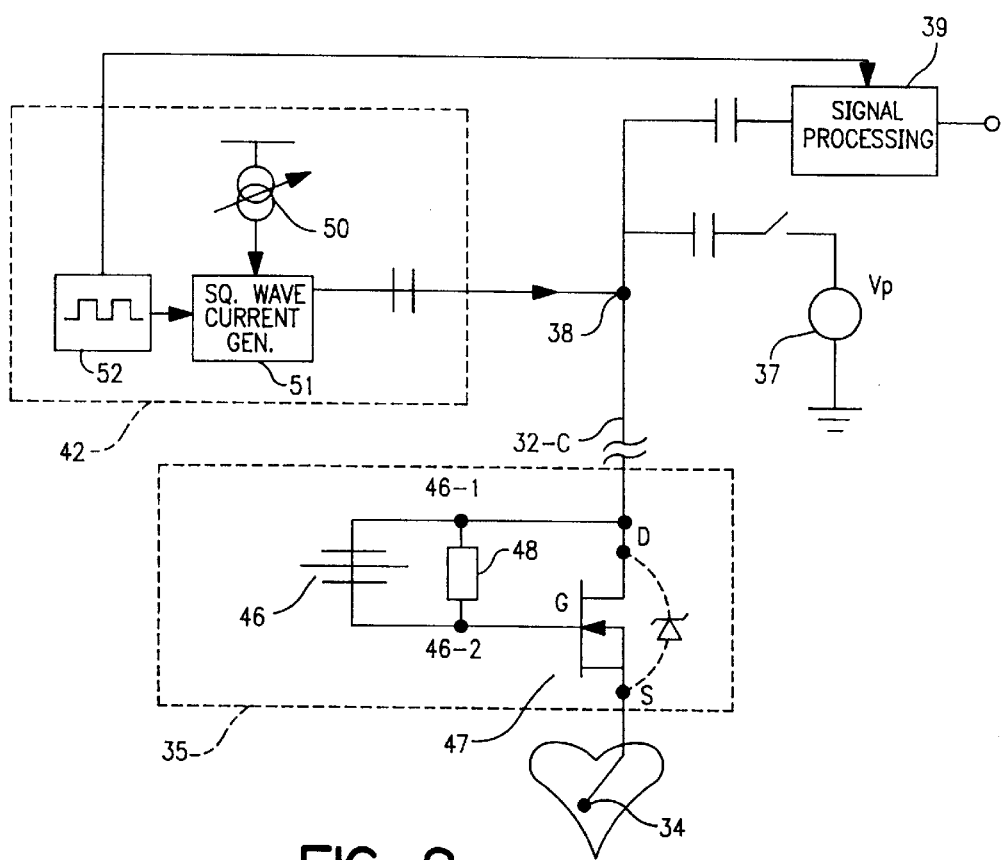
FIG. 2 is a circuit diagram showing the combined sensor and switching device in the lead, together with circuitry in the pacemaker for providing a multiplexing signal to the lead, and also for signal processing and for delivering pacing stimuli.

Referring now to FIG. 2, there is shown a circuit diagram of the primary novel elements of a preferred embodiment of this invention. A lead 32 has a conductor 32-C which is connected toward the distal region of the lead to the elements within block 35, which elements are combined to provide multiplexed delivery of pressure signals from piezoelectric element 46 along with cardiac signals picked up at tip electrode 34. Also shown are the circuit elements located in the implanted pacemaker which are pertinent to the multiplexing operation of the lead signals.

Referring specifically to the circuit elements within block 35, element 46 is preferably a piezoelectric element of conventional form, which responds to sensed pressure variations by providing a voltage across its terminals which is reflective of pressure variations in the patient's heart, e.g., the right ventricle or right atrium. It is to be noted that this invention is not limited in terms of the characteristics of this sensor, and indeed other sensors in addition to pressure sensors are equally adaptable for use in this invention. For example, certain accelerometer-type sensors may be used in combination with a suitable switching device 47. Also, it is to be understood that the term "switching device" is used in the context of the circuit application, and includes MOSFETS which are operated in different modes, including a linear mode.

A switching device 47, illustrated as an N MOSFET, is connected so that its drain (D) is connected to a first terminal 46-1 of element 46; its gate (G) is connected to the other terminal 46-2; and its source (S) is connected directly to tip electrode 34. A large value resistance 48, suitably a reverse diode providing giga-ohms, is connected across the piezoelectric element. The characteristic of such a switching element is that when a positive current is supplied from lead 32, providing a positive voltage from terminal 46-1 to terminal 46-2, the gate to source charges up through the high resistor 48, to the point where threshold for conduction is reached at about 0.8 volts. At this point, the gate to source diode conducts, with a voltage across it of approximately 0.8 volts which is maintained as long as the positive current flows. When the current is switched in the negative direction, i.e., from source to drain through the N MOSFET, the N MOSFET 47 provides an effective forward biased diode (as shown in dashed lines) from source to drain, giving an output of about −0.5 volts from drain to source. Thus, when AC coupled current is positive, the N MOSFET is biased in a normal mode and the sensor voltage developed across the piezo element is connected in series through the gate to source path to the tip electrode. Under these circumstances, the voltage with respect to ground that appears on the conductor is the combination of any cardiac signal voltage appearing at tip 34, plus the gate-to-source voltage (of approximately 0.8 volts, plus the sensor voltage across element 46. Conversely, when the current is negative, the sensor element 46 is essentially isolated, and only the cardiac signal developed at tip 34 plus the forward biased source to drain voltage is connected through to the conductor 32-C. Thus, for the positive half of each constant current cycle, there is delivered to the lead conductor the cardiac signal plus the pressure signal plus a first DC voltage; and during each negative half cycle of the current signal, there is delivered to the conductor simply the cardiac signal plus a second DC voltage. By suitably processing the signals connected on the conductor to terminal 38, indicated in block 39, the respective cardiac signals and sensor information can be separated out.

Still referring to FIG. 2, there is illustrated the circuitry 42 within the implanted pacemaker for providing the alternating current drive signal, as well as the circuitry 39 for processing the signals transmitted back from the lead and for delivering cardiac stimulus pulses. Square wave signal generator 52 provides a square wave output, suitably a 5 kHz signal. This is connected to a square wave generator 51, which receives a constant current input from constant current generator 50. By setting the output of current generator 50 at 20 microamps, and using a conventional switching arrangement, there is provided a square wave of ±20 microamps, which is coupled to conductor 32-C at terminal 38. The use of low level AC to drive the piezo device provides the multiplexing and incorporates a safety feature compared to arrangements which use a DC drive signal. By adjusting the output of current generator 50, lower current levels can be attained. Furthermore, during any time when the pressure sensing function is not desired, the generator output can be reduced to zero by programming the current level from adjustable source 50. Output stimulus pulses for pacing are delivered from voltage generator 37, and switched into connection with the lead 32 under control of the timing circuitry enclosed within block 40 (illustrated in FIG. 1). Also, the signals generated at the output of circuitry block 35 are connected to signal processing circuitry 39, which receives a clock input from signal generator 52.

Figure 3:
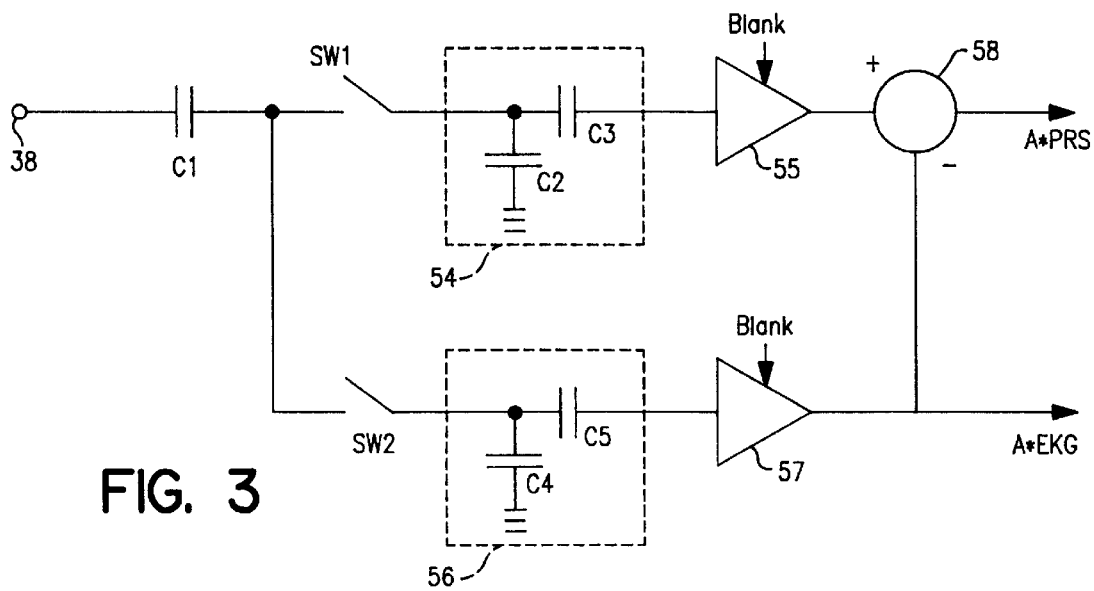
FIG. 3 is a circuit diagram showing the processing circuitry for recovering the respective sensor signals and cardiac signals.

Referring now to FIG. 3, there is shown a circuit diagram for processing the information delivered from the tip/sensor network 35. The signals are inputted at node terminal, and are coupled through capacitor C1 to respective switches designated SW1 and SW2. The channel comprising SW1 is the channel for carrying the cardiac (EKG) and pressure (PRS) signals, while the channel including SW2 carries simply the EKG, or cardiac signal developed during the negative half of each current drive signal. When SW1 is closed, SW2 is open; the signal through SW1 is connected through filter 54, illustrated as comprising capacitors C2, C3, selected to block out the DC variation and present only the modulation signals to the input of amplifier 55. Amplifier 55 is suitably blanked, as shown, whenever a pacemaker pulse is delivered from generator 37. Thus, the output of amplifier 35 is a gain factor times the combined EKG and PRS signal. Referring to the second channel, SW2 is closed during negative excursions of the drive signal and opened during positive excursions, thus providing the multiplexed portion of the signal which contains only the cardiac EKG information. This signal is passed through filter 56, shown as comprising capacitors C4, C5 and amplified at amplifier 57 to provide an output which is the gain factor times simply the EKG signal. The channels are balanced, ,such that the gain factors are made to be essentially equal. An adder circuit shown at 58 is connected to subtract the output from amplifier 57, so as to cancel out the EKG signal and provide simply the PRS signal as a first output. The output from amplifier 57 is taken directly to provide the cardiac, or EKG signal.

Figure 4A:
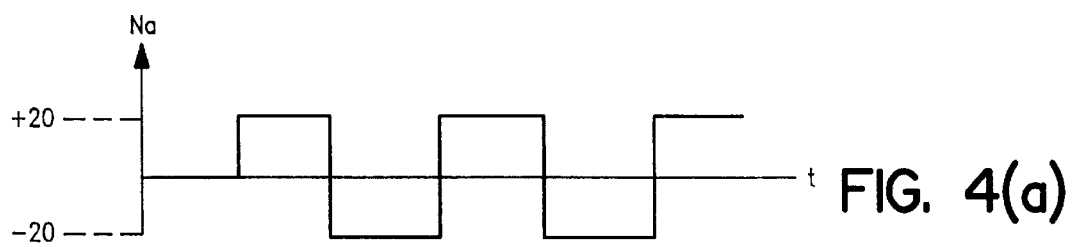
FIG. 4 is a series of timing diagrams illustrating operation of the multiplexing single conductor arrangement of this invention.
Figure 4B:
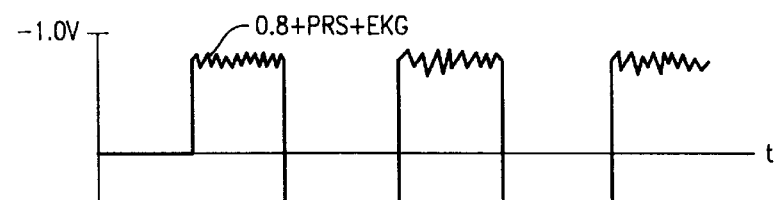
Figure 4C:
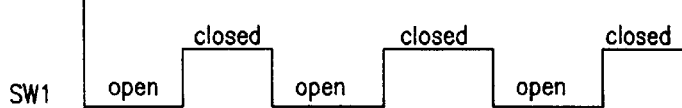

Referring now to FIG. 4, there are shown timing diagrams which are useful in interpreting the operation of this invention. The current generator is shown in FIG. 4(a), providing alternate +20 and -20 microamp constant currents, suitably at a rate of about 5 kHz. During the positive current pulses, and as illustrated in FIG. 4(b), the positive voltage of approximately 0.8 is developed between the gate and the source of device 47, and the EKG and pressure sensor signals modulate that voltage which is connected to terminal 58. As seen in the two curves of FIG. 4C, when the current source is positive, SW1 is closed and SW2 is open, so that the first, or EKG plus PRS channel only is receiving the signal input which appears at terminal 38. When the current generator goes negative SW1 is open and SW2 is closed, such that only the second channel is receiving the input. The signal appearing at terminal 38 drops negative, as seen in FIG. 4(b), and is substantially a -0.5 volt signal, modulated only by the EKG signal.

It is to be understood that the single conductor feature of this invention can be used with different pacing systems. Thus, it can be used with a unilateral system where the lead need have only one conductor; or it can be used with a bipolar system, or other plural chamber systems, where one or more additional lead conductors are employed for other reasons. For example, two or more "single" conductor leads can be used in two or more respective heart chambers.

It is to be understood that the "single conductor" feature of this invention can be used with different pacing systems. Thus, it can be used with a unipolar system where the lead need have only one conductor; or it can be used with a bipolar system, or other plural chamber systems, where one or more additional lead conductors are employed for other reasons. For example, two or more "single" conductor leads can be used in two or more respective heart chambers. In each of these embodiments, the invention is characterized by a sensor and a two-state, or two-mode switching-type circuit housed in the lead; the switching-type circuit is driven into alternate states, or modes, by the AC current signal generated in the pacemaker.

We claim:

1. An implantable cardiac pacing system for pacing a patient's heart, having a pacemaker and a lead, said lead comprising a proximal end connected to said pacemaker and a distal end, a casing running the length of said lead for enclosing said lead, a tip electrode at about said lead distal end, a sensor mounted within said casing at a predetermined location so that both said tip electrode and said sensor are positionable within said heart, a conductor extending within said casing from said proximal end to said location, and connecting means for connecting said conductor respectively to said sensor and to said tip electrode, and said pacemaker comprising multiplex means connected to said conductor at said lead proximal end for obtaining cardiac signals connected from said tip electrode and sensor signals connected from said sensor.

2. The system as described in claim 1, wherein said pacemaker comprises pulse means for delivering pacing pulses to said conductor, and wherein said connecting means has means for transmitting said pacing pulses to said tip electrode.

3. The system as described in claim 2, wherein said lead is a unipolar lead and said pacemaker has a case which is connected as an electrode, whereby said lead has only one conductor.

4. The system as described in claim 1, wherein said sensor is a piezoelectric pressure transducer.

5. The system as described in claim 1, wherein said connecting means comprises electronic switching means for alternately switching said sensor into and out of an electrical path between said tip electrode and said conductor, and for switching said tip electrode directly to said conductor when said sensor is switched out of said path.

6. The system as described in claim 5, wherein said switching means comprises an N MOSFET.

7. The system as described in claim 5, wherein said multiplex means comprises current source means for delivering an alternating current to said conductor, said alternating current driving said switching means to alternately switch said sensor.

8. The system as described in claim 7, wherein said multiplex means comprises signal processing means for processing signals on said conductor to derive said cardiac and sensor signals.

9. The system as describe in claim 8, wherein said signal processing means comprises first and second channels, and second switching means for switching said first channel to said conductor when said sensor is switched into said path, and for switching said second channel to said conductor when said tip electrode is switched directly to said conductor.

10. A pacing system having a pacemaker and a lead, said lead comprising:

a proximal end and a distal end, and a casing extending from said proximal end to said distal end, a tip electrode at about said distal end, a sensor located at a position within said casing near said distal end, a conductor extending within said lead casing from said proximal end to said sensor position, a switchable connecting circuit means for switchably connecting said tip electrode alternately through said sensor to said conductor and directly to said conductor, and said pacemaker comprising switching drive means for providing a drive signal to said conductor for switching said connecting circuit means, and signal processing means connected to said conductor for processing the signals on said conductor so as to derive respective signals representative of cardiac signals sensed at said tip electrode and sensor signals generated by said sensor.

11. The system as described in claim 10, wherein said sensor is a pressure sensor for sensing intracardiac pressure, and said lead has only one electrode and only one conductor.

12. The system as described in claim 10, wherein said connecting circuit is a two-state circuit and said drive means comprises means for producing an alternating signal which drives said connecting circuit alternately to its two different states.

13. The system as described in claim 12, wherein said connecting circuit comprises a MOSFET type element.

14. The system as described in claim 12, wherein said drive means comprises an AC constant current source.

15. A pacing lead for use in a pacing system having a pacemaker for generating pacing pulses, said lead comprising:

a lead body having a proximal end and a distal end and a casing running the length of said body, a tip electrode at about said distal end, a transducer element at a location within said casing near said distal end for obtaining signals representative of a cardiac parameter, a conductor providing an electrical connection from said proximal end to about said location, a two state connecting means connected to said transducer element and to said tip electrode for connecting said transducer in electrical connection with said tip when it is in a first of said states, whereby a signal carrying information representative of said parameter is connected to said conductor, and for isolating said transducer element and connecting said tip electrode directly to said conductor when it is in a second of said states, whereby a signal carrying information representative of a cardiac signal sensed at aid tip electrode is connected to said conductor.

16. The lead as described in claim 15, wherein said connecting means comprises a two-mode device which is switchable to either one of said modes as a function of the current driven through it.

17. The lead as described in claim 15, wherein said transducer element is a pressure sensor, and said connecting means comprises a MOSFET device.

18. An implantable cardiac pacing system for pacing a patient's heart, having a pacemaker and a lead, said lead comprising a sensor and a tip electrode, a conductor providing an electrical connection substantially the length of said lead, and a switchable connecting means for connecting said tip electrode to said conductor through a first path which includes said sensor or through a second path that does not include said sensor, and wherein said pacemaker comprises drive means for delivering a drive signal to said conductor that controls said connecting means to connect said tip electrode alternately through said first and second paths.

19. The system as described in claim 18, wherein said pacemaker comprises detect means for detecting a signal from said sensor when said connecting means connects said tip electrode through said first path, and for detecting a signal from said tip electrode when said connecting means connects said tip electrode through said second path.

20. The system as described in claim 18, wherein said drive means comprises an AC constant current generator, and said connecting means comprises a switchable semiconductor element.

\* \* \* \* \*